United States Patent [19]

Coombs

[11] Patent Number: 4,808,157

[45] Date of Patent: Feb. 28, 1989

[54] MULTI-LUMEN EPIDURAL-SPINAL NEEDLE

[75] Inventor: Dennis W. Coombs, Etna, N.H.

[73] Assignee: Neuro Delivery Technology, Inc., Tempe, Ariz.

[21] Appl. No.: 72,428

[22] Filed: Jul. 13, 1987

[51] Int. Cl.⁴ .............................................. A61M 5/32
[52] U.S. Cl. ...................................... 604/44; 604/52; 604/158; 604/272
[58] Field of Search .................................... 604/43–44, 604/51–53, 158–169, 272–274

[56] References Cited

U.S. PATENT DOCUMENTS

| | | | |
|---|---|---|---|
| 2,922,420 | 1/1960 | Cheng | 604/272 |
| 4,134,402 | 1/1979 | Mahurkar | 604/44 |
| 4,645,491 | 2/1987 | Evans | 604/158 |

FOREIGN PATENT DOCUMENTS

| | | | |
|---|---|---|---|
| 834211 | 9/1976 | Belgium | 604/44 |
| 818246 | 10/1951 | Fed. Rep. of Germany | 604/44 |
| 624618 | 9/1978 | U.S.S.R. | 604/160 |

Primary Examiner—Dalton L. Truluck
Attorney, Agent, or Firm—Michael J. Weins; Janine J. Weins

[57] ABSTRACT

The needle of the present invention is a multi-lumen needle and preferably a dual-lumen epidural-spinal needle. The needle of the present invention is provided with a hub, which allows for attachment of a syringe to one or more of the lumina, or alternatively the attachment of an adapter to which a syringe can be attached. Preferably the lumina have different cross sectional areas. The smaller of the lumina should be of sufficient size to allow a spinal neelde, guide wire, or microcatheter to be inserted through the lumen. The larger of the two lumina should preferably be of sufficient size to allow an epidural catheter, spinal needle or guide wire to be introduced. The needle of the present invention has applications of regional anesthesia, chronic and post operative pain management, cricothyroid puncture, intracerebroventricular puncture and, access and drainage of concealed fluid collections within the body.

10 Claims, 5 Drawing Sheets

MULTI-LUMEN EPIDURAL-SPINAL NEEDLE

FIELD OF INVENTION

The present invention is directed to a multi-lumen needle and in particular to a dual-lumen epidural-spinal needle earlier described in Disclosure Document No. 170,906 dated May 29, 1987.

BACKGROUND

Punctures of the spinal area are required in conjunction with a variety of medical and surgical procedures. Frequently medication, and in particular, epidural and spinal anesthesics must be introduced through a needle or a catheter. It may be desirable to both introduce medication in the vicinity of the puncture through a spinal needle and to introduce medication through a catheter to a location remote from the puncture in the epidural or spinal spaces.

Using prior art techniques, multiple punctures would have to be made for simultaneous introduction of an epidural catheter and a spinal needle, or for the introduction of two epidural and/or spinal catheters. Multiple spinal punctures have greater risk than a single puncture because of the increased trauma from additional punctures and because the time required to perform the procedure must be extended.

The present invention is directed to a new and improved multi-lumen needle, and in particular a new improved epidural-spinal needle. The needle of the present invention allows for location and cannulation of the epidural space, the introduction of a spinal needle, the introduction of spinal or epidural catheters, or the introduction of multiple catheters through a single puncture.

A number of prior art patents teach epidural needles, spinal needles and methods of introducing epidural catheters.

U.S. Pat. No. 4,141,365 teaches an epidural needle which can be used for introducing a lead electrode or catheter.

U.S. Pat. No. 4,518,383 teaches a co-axial needle in which both lumina are concentric and share a common axis. The needle of the '383 patent has a tapered end and is provided with a stylet to reduce coring. The needle of the '383 patent can be used for either administering epidural or spinal anesthesia, but can not be used for the administration of such simultaneously.

U.S. Pat. No. 4,349,023 teaches details of an adapter which can be applied to an epidural needle to assist in the introduction of a catheter.

Spinal anesthesia frequently requires the initial administration of small quantities of an anesthetic agent into the subarachnoid space. Since spinal anesthesia may be effective for only short periods of time, an adjunctive epidural anesthetic technique that can be continuous may be required for longer surgical procedures. Alternatively, either continuous epidural or spinal techniques must be utilized. The epidural technique yields a less dense local anesthetic block, while the spinal technique can lead to equally undesirable consequences including post spinal headache. Significant advantages could be obtained if the epidural and spinal procedures could be combined.

A procedure using conventional prior art single lumen needles to administer the spinal and epidural anesthetic requires the procedures either be performed at separate sites, or the two procedures be separated by a time interval. It would be advantageous and would reduce trauma if both procedures could be carried out nearly simultaneously at the same site utilizing small gauge spinal needles. If both procedures were carried out simultaneously utilizing one puncture the length of the procedure, and the discomfort to the patient would be reduced.

One option for using a single needle is to use a Touhy needle to locate the epidural space and then to insert a spinal needle through the Touhy needle to such an extent that the spinal needle penetrates the dura. An anesthetic agent can then be administered through the spinal needle. The spinal needle can then be withdrawn, leaving the Touhy needle in position for use in introduction of an epidural catheter in the usual way. This technique may have a significant risk in that the epidural catheter will pass into the subarachnoid space through the dural perforation and be undetected. Also the immediate epidural catheterization is not assured.

If a single needle is not used for the administration of the spinal and epidural anesthetic, but rather multiple needles are used, multiple punctures must be made in separate locations. One puncture is used for the insertion of, and to guide the spinal needle while the other puncture is used for the introduction of a catheter or for the introduction of a second needle.

If combined spinal and epidural anesthesia is to be used, the time to complete the epidural cannulation must be minimized once the spinal anesthetic is injected since a dangerous situation may occur such as serious drops in blood pressure and/or pulse rate once the spinal anesthetic has been administered. This dangerous situation may arise during performance of the epidural catheterization since using prior art techniques epidural catheterization must be performed subsequent to the spinal anesthetic injection unless multiple needles and multiple punctures are used.

The present invention is directed to a needle which will allow for the simultaneous introduction of one or more needles, a needle and a catheter, or multiple catheters through a single skin puncture. Thus the present invention has advantages with respect to the prior art by reducing trauma, reducing procedure time, and providing the practitioner with a greater flexibility regarding the positioning of the catheters and needles for a specific procedure since the needle of the present invention can function as an introducer.

SUMMARY OF THE INVENTION

It is an object of the present invention to provide a needle which can be used to simultaneously perform spinal and epidural cannulation and/or catheterization.

It is another object of the present invention to provide a needle which can be used to simultaneously administer epidural medication such as an anesthetic and be used to insert an epidural catheter.

It is an object of the invention to provide a needle through which it is possible to simultaneously administer medication to two separate areas such as the lumbar epidural space and lumbar intrathecal space.

It is an object of the invention to provide a needle through which it is possible to simultaneously administer medication to two separate areas without intermixing the medications.

It is another object of the present invention to provide a needle which can be used to simultaneously administer medication while a catheter is placed in either the epidural or the intrathecal space.

It is another object of the invention to provide a needle which allows two medicines to be administered without intermixing.

It is yet another objective of the present invention to provide a needle which allows medication to be transported by separate passages and/or catheters into separate regions of the body.

It is an object of the present invention to provide a needle through which a spinal tap and spinal anesthetic/analgesic can be initiated at any time after the epidural space has been identified.

It is an object of the present invention to provide a needle through which either a preliminary epidural injection, or placement of an epidural catheter can be performed before or after a spinal tap is initiated.

It is an object of the present invention to reduce the risk of undetected cardiovascular hypotension during initiation of combined epidural and spinal anesthesia.

It is an object of the present invention to reduce the number of skin and/or spinal punctures for a given procedure.

It is an object of the present invention to reduce the incidence of spinal headache by facilitating the introduction and use of smaller spinal needles having a gauge size equal to or less than 26 gauge.

These and other objects of the present invention will become apparent from the following figures and description.

The present invention is directed to a multi-lumen needle and in a preferred embodiment to a dual-lumen epidural-spinal needle.

The needle of the present invention in its simplest form has two lumina. The lumina terminate in a point and in a hub. The axes of the lumina are parallel except near the hub where the lumina diverge so as to provide easier access to each of the lumen passages, and optionally near the point where the axes may diverge so as to direct a catheter along a path nearly perpendicular to the needle insertion path.

Preferably the hub allows for the attachment of one or more conventional syringes.

Preferably the termination of the lumina in the hub is such that a spinal needle and/or a catheter can be passed into and through each of the lumen.

Preferably the hub is provided with a flange which can be readily grasped and used to guide and position the needle.

In another preferred embodiment the hub flange is provided with extensions which allow the needle to be readily grasped, positioned and inserted.

Preferably the needle of the present invention is provided with stylets to reduce coring during insertion.

In a preferred embodiment of the present invention the point of the needle is so contoured that the needle can be rotated 360° with a minimum of coring and dragging of material.

Preferably the lumina have different cross sectional areas. The smaller lower lumen can be used as an introducer for a spinal needle used to perform a spinal tap. Thus the smaller of the lumina, or spinal lumen is preferably of sufficient size to allow for insertion of a spinal needle or microcatheter.

Preferably the larger lumen terminates at the hub in an attachment or an adapter for a syringe, while the termination of the smaller lumen is provided with a protuberance. The protuberance should be contoured so as to be readily felt and to serve as a locator and guide for the insertion of a spinal needle even in the event that the entrance to the smaller lumen cannot be visually observed and thus the spinal needle cannot be visually aligned for insertion.

In another preferred embodiment of the present invention the lumina terminate in a hub which is color coded in such a manner that needles having different sizes and/or different point configurations can be readily distinguished.

In yet another preferred embodiment of the present invention the needle is encased in a polymeric material selected to facilitate easy insertion and positioning of the needle.

Preferably the larger lumen, or epidural lumen is no larger than required for insertion of a catheter. The larger lumen, or epidural portion of the multi-lumen needle should have a gauge size less than 14 gauge and preferably between approximately 16 and 20 gauge and preferably about 18 gauge.

The needle of the present invention allows for the administration of both epidural and spinal anesthesia almost simultaneously. The simultaneous administration of epidural and spinal anesthesia reduces the risk of undetected hypotension associated with the administering of a spinal anesthesia prior to, or during, epidural catheterization.

The needle of the present invention can serve as an introducer for very small spinal needles of 26 to 32 gauge. The small spinal needle can in turn be used for a spinal puncture or microcatheters can be inserted intrathecally through the small gauge spinal needle.

Preferably the lumen of the present invention terminate in a Hustead point. Optionally the epidural and spinal needles are rotated 180° with respect to their axes so that two Hustead points combine to form a wedge point. The wedge point aids in the insertion, positioning and repositioning of the needle.

BEST MODE FOR CARRYING THE INVENTION INTO PRACTICE

Figure 1:
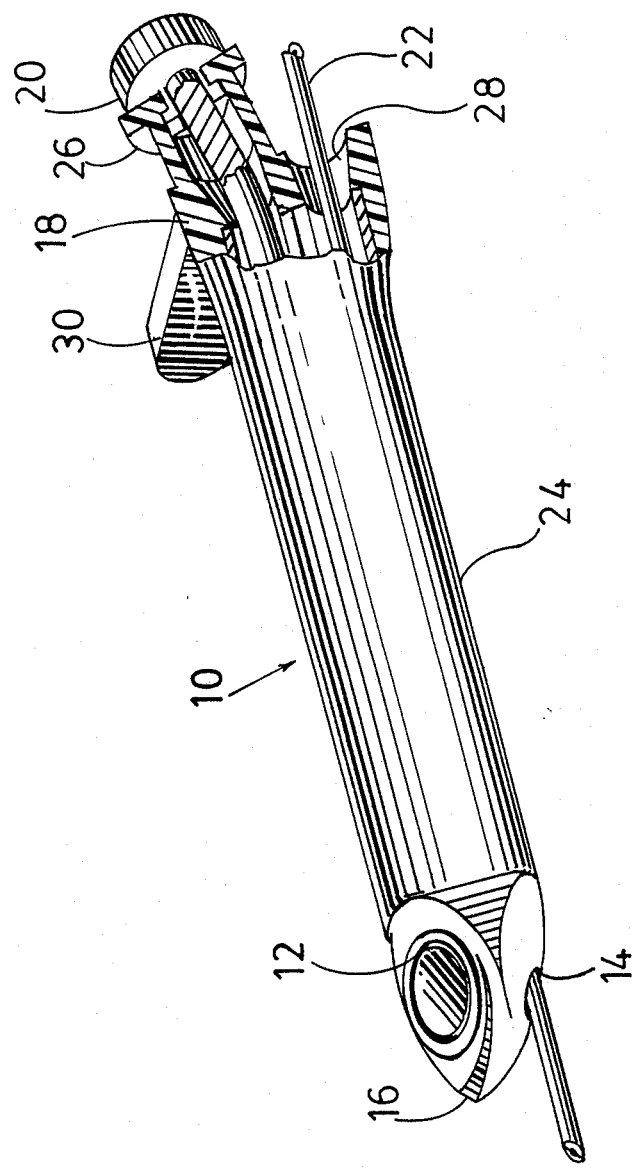
FIG. 1 is a schematic representation of one embodiment of the present invention in which a stylet is positioned in the larger, or epidural lumen and a spinal needle is positioned in the smaller, or spinal lumen. A portion of the needle hub has been cut away to show details of the path taken by the spinal needle and stylet. The entire needle assembly is encased in a smooth polymeric material.

FIG. 1 is a schematic representation of one embodiment of the epidural-spinal needle of the present invention. The needle 10 has a first lumen 12 and a second lumen 14. The lumina are positioned in an over under relationship and terminate in a point 16 and a hub 18.

Preferably the lumina are of different size with the larger, or epidural lumen 12 being of sufficient size to accommodate an epidural catheter, and the smaller or spinal lumen 14 being of sufficient size to permit passage of a spinal needle.

The walls of the lumina are bonded and terminate in a point 16. The point preferably has the configuration of a standard or modified Touhy or Hustead tip.

The nominal cross section of the needle 10 is oval or elliptical, while the preferred cross section of each of the lumina is circular. Preferably each of the lumina is between 14 and 32 gauge. More preferably the needle 10 should have a maximum cross-sectional dimension equal to, or less than, the diameter of a 14 gauge needle with the larger epidural lumen 12 between about 16 to 20 gauge and the smaller spinal lumen 14 between about 20 and 24 gauge.

The point 16 preferably has a modified Touhy configuration so that a catheter which may be passed through the lumina will be directed away from the lumina axes.

A stylet 20 is positioned in the epidural lumina 12. The stylet 20 avoids coring of body tissue and fluids during insertion of the needle 10.

A spinal needle 22 is positioned in the second lumen 14. The spinal needle 22 allows penetration into the tissue beyond the point 16.

The needle 10 is encased in a hard smooth plastic or polymeric sheath 24. The sheath 24 provides a smooth continuous exterior surface and can serve as to maintain the proximate relationship of the needle components, the epidural lumen 12, the spinal lumen 14 and the hub 18. Optionally a partial plastic sleeve could be provided to cover the lumina.

A syringe adapter 26 for attachment of a syringe is provided to the hub 18 at the termination of the upper epidural lumen 12. The hub 18 is provided with an enlarged opening 28 in the vicinity of the termination of the spinal lumen 14. The enlarged spinal lumen opening 28 allows the spinal needle 22 to be easily inserted and directed.

Preferably the syringe adapter 26 is provided with index marks which allow the stylet 20 to be positioned so that the tip of the needle 16 presents a smooth surface. A smooth tip 16 minimizes coring during insertion of the needle 10.

Preferably flanges 30 are provided to the hub 18. The flanges 30 allow the needle to be grasped and positioned.

Figure 2:
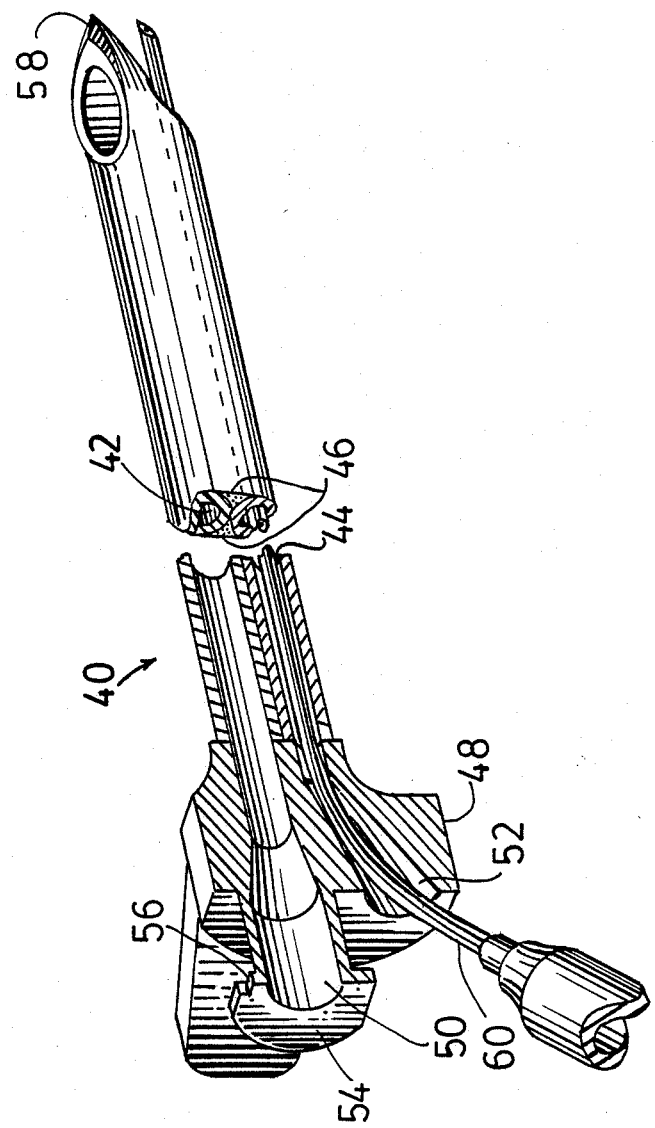
FIG. 2 is a schematic representation of another embodiment of the present invention. A portion of the hub and the lumina has been cut away to show details of the hub structure and the proximity of the lumen passages. The walls of the lumina are maintained in intimate contact by welding.
Figure 3:
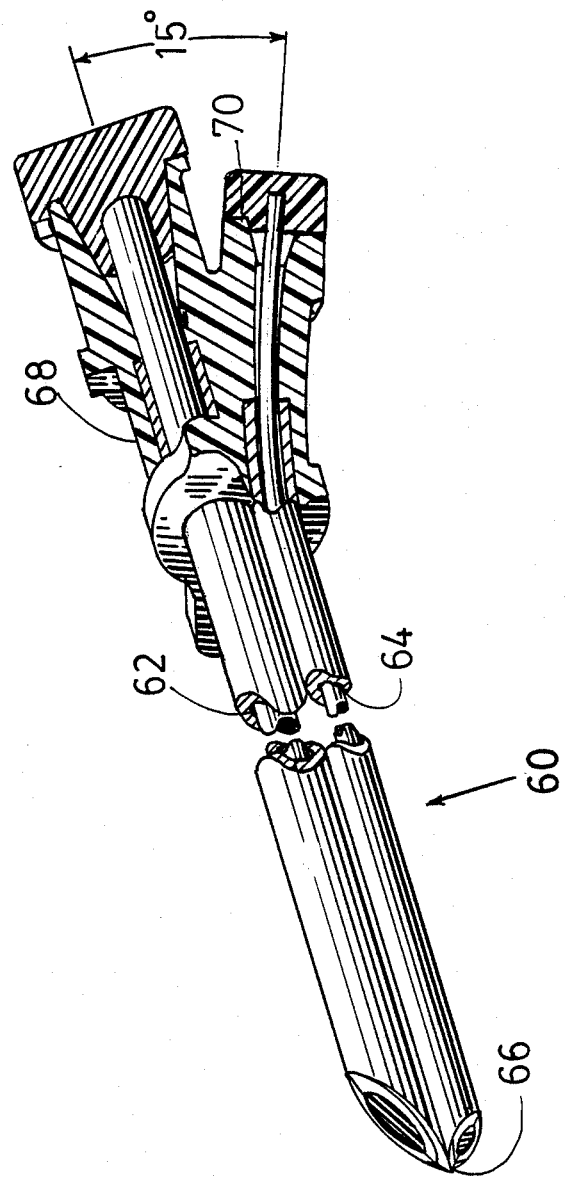
FIG. 3 is a schematic representation of an embodiment of the present invention in which the wedge points of a spinal and an epidural needle have been rotated with respect to each other by 180 degrees and positioned so as to provide a centrally disposed chisel point. The hub of this particular embodiment is provided with two different lumen entrance configurations. The epidural hub entrance is provided with a flange so that a syringe can be attached. The hub configuration at the entrance to the spinal lumen is provided with a hub extension such that the entrance can be readily detected by feel even if view is blocked by a syringe attached to the epidural hub entrance. Stylets have been positioned in both lumina to limit coring during insertion.

Preferably the lumen passages diverge at the hub 18 as is shown in FIGS. 2 and 3. This divergence allows for easier insertion of devices into the lumina.

FIG. 2 is a representation of a second embodiment of the epidural-spinal needle 40 of the present invention. The walls of the epidural lumen 42 and the spinal lumen 44 are connected by means of welded seams 46. Preferably the welds form a continuous smooth seam.

The lumina terminate in a hub 48. The hub 48 is provided with a first passage 50 which mates with the first lumen 42 and a second passage 52 which mates with the second lumen 44. The first passage 50 and the second passage 52 diverge so as to separate the entrances to the lumina.

Communicating with the first passage 50 and extending away from the hub 48 is a syringe adapter 54. The syringe adapter 54 allows a conventional syringe, not shown, to be attached. The syringe communicates with the epidural lumen 42 through the passage 50.

The syringe adapter 54 is provided with an indexing mark 56. The indexing mark 56 can be used to indicate the position of the tip 58 and to position a stylet so that the stylet forms a smooth tip surface so that coring will not occur during insertion of the needle 40.

The size of the epidural lumen 42 is such that it can accommodate the desired flow from a syringe, or alternatively an epidural catheter can be inserted into and through the lumen and directed into the epidural space.

The size of the spinal lumen 44 is such that a spinal needle 60 can be passed through the second lumen 44.

The hub 48 can be made of a metal or polymeric material.

FIG. 3 shows an epidural spinal needle of the present invention in which two stylets are positioned in the lumina. In this embodiment the needle 60 has a first lumen 62 and a second lumen 64. The lumina terminate in a point 66 which is formed by the merger of two Hustead points so as to form a wedge configuration. Electron beam welding or laser welding can be utilized to bond the walls of the lumina.

The epidural-spinal needle 60 is provided with a hub 68. The hub 68 forces the lumina to diverge. The lumina should diverge to provide a sufficient separation that easy access can be gained to either lumen. The divergence is preferably approximately 15 degrees and occurs over approximately one fourth of the length of the needle. If the divergence is greater than 15 degrees it will be difficult to advance a spinal needle in the spinal lumen 64. The divergent end of the first lumen 62 and the second lumen 64 are affixed to the hub 68. A protuberance 70 is provided to the hub 68 and contoured so as to be readily felt and thus to serve as a locator and a guide for insertion of a spinal needle even in the event that the entrance to the smaller lumen cannot be visually observed and thus the spinal needle cannot be visually aligned for insertion.

A hub 68 encloses the divergent portion of the first lumen 62 and the second lumen 64. Indexing information and information relating to the size of the lumina and the particular point configurations can be encoded on the hub 68. When a polymeric hub is used such information can be included by color coding the polymer.

Figure 4:
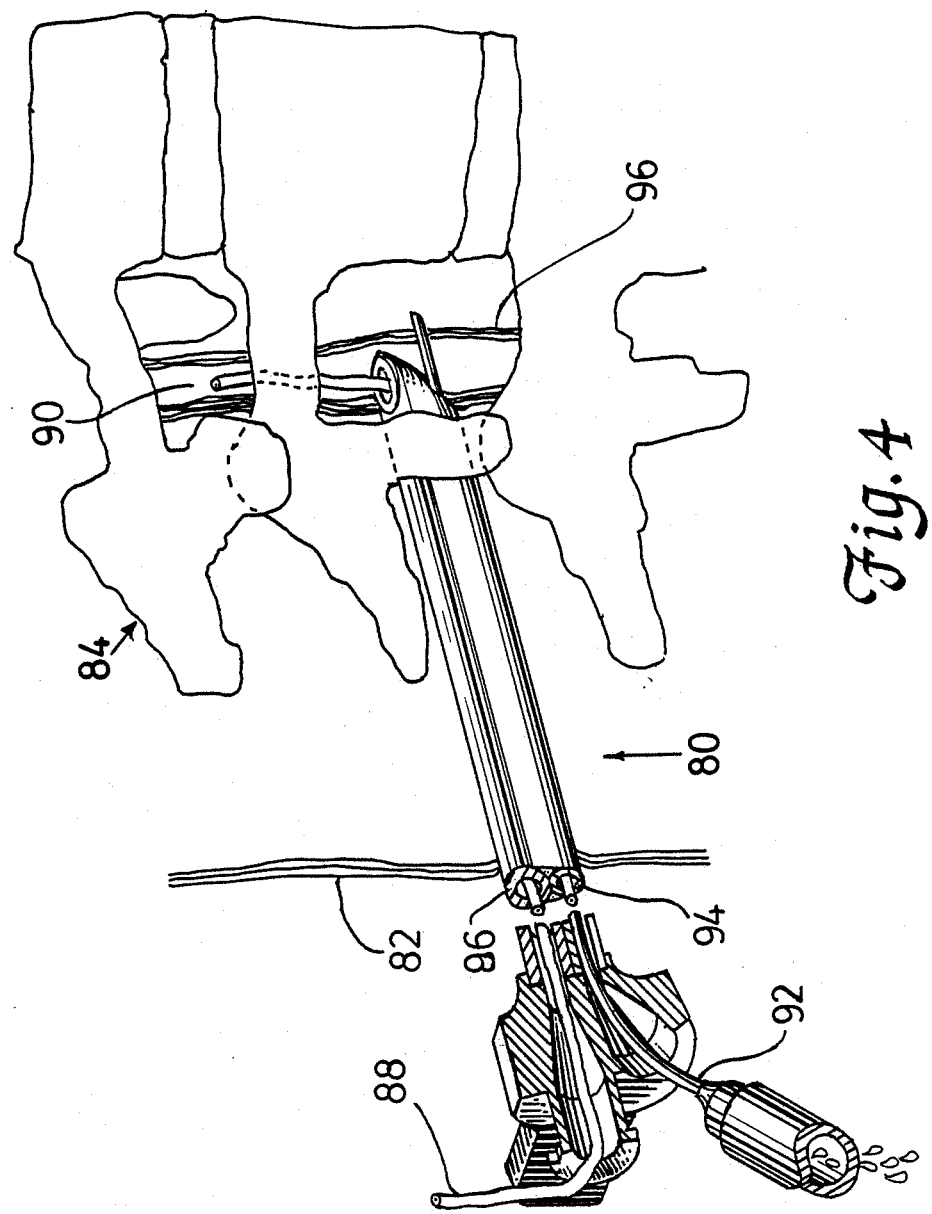
FIG. 4 is a schematic representation of the needle of the present invention positioned in the spinal region. A catheter has been placed through the epidural lumen and is positioned in the epidural space. A spinal needle passed through the spinal lumen has penetrated the dura.

FIG. 4 is a schematic illustration of the epidural-spinal needle 80 of the present invention positioned for use. The epidural-spinal needle 80 passes through the skin 82 and into the spinal column 84. Preferably the two lumina are welded in such a way that between them is a continuous and smooth seam. A catheter 88 is shown inserted in the epidural space 90. The tip of the larger or epidural lumen is positioned so that the termination or exit of the lumen would direct a catheter cephalad into the epidural space. In this mode it is possible to administer anesthesia through the catheter 88 and to extract spinal fluids or administer spinal anesthetics through the spinal needle 92. The catheter 88 is shown inserted through the epidural lumen 86 cephalad into the epidural space 90. A spinal needle 92 is passed through the spinal lumen 94 and exits penetrating the dura 96. A spinal catheter could be passed intrathecally at this point through the introducing spinal needle.

Figure 5:
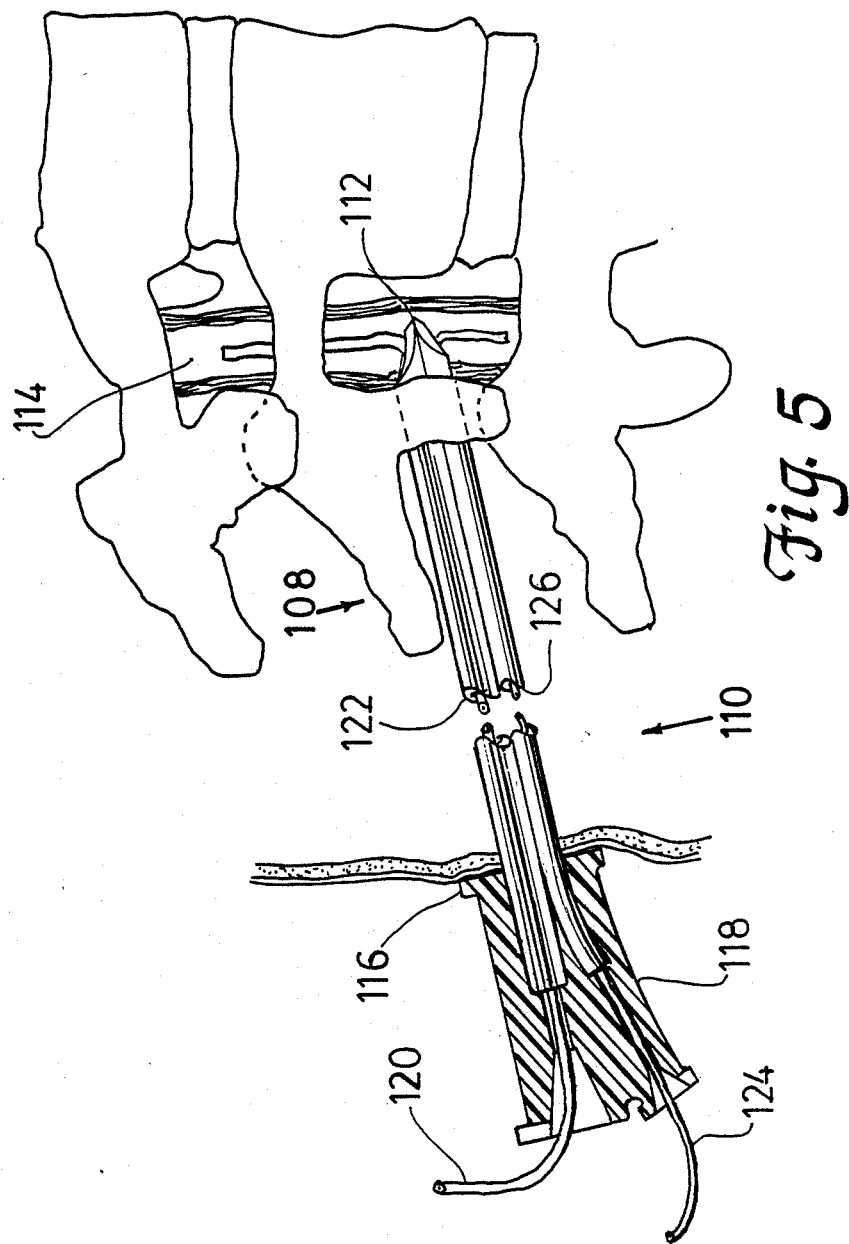
FIG. 5 is a schematic representation of the embodiment of the needle of the present invention shown in FIG. 3 positioned in the spinal region. Two catheters have been passed through the lumina and are positioned in the epidural space. Catheterization of the epidural space both above and below the position at which the needle was inserted is shown.

FIG. 5 shows the needle of FIG. 3 inserted in the spinal column 108. The needle 110 is positioned such that the needle tip 112 is in the epidural space 114. Stop 116 on the hub 118 on the needle 110 limits the depth of penetration of the needle tip 112 and avoid separation of skin by the diverging lumina.

When the needle is positioned, an upper catheter 120 can be inserted into the upper lumen 122 to be positioned so as to provide medication to a site above the needle tip 112. A lower catheter 124 can be inserted in the lower lumen 126 and positioned so as to provide medication to a site below the needle tip 112, yet still in the epidural space 114.

The Multi-Purpose Epidural-Spinal Needle has particular utility for the administration of spinal and/or epidural anesthesia. Using the needle of the present invention anesthesia may be provided independently, concurrently or sequentially to the spinal and/or the epidural regions.

The needle of the present invention when inserted may also be used as a spinal needle guide or introducer to sample the cerebro spinal fluid contained in the subarachnoid space while the needle is simultaneously used to insert catheters into the epidural and/or intrathecal spaces.

The interior surface of the lumina should be smooth to facilitate the ready insertion of a needle and catheters.

Using the epidural-spinal needle of the present invention conventional technology such as the loss of resistance method can be used to locate the epidural space.

The Multi-Purpose Epidural-Spinal Needle of the present invention is contoured in such a manner that the distal end or tip bends shortly before the termination of the needle at a 90 degree angle to the tracking path of the epidural needle. By bending the direction of the lumen in this manner, the epidural-spinal needle after insertion is so contoured as to facilitate the introduction and cephalad direction of an epidural catheter upward and parallel to the spinal cord. Alternatively the assembly can be introduced upside down, and the epidural catheter may be directed downward or caudally in the epidural space.

The needle of the present invention is particularly well suited for providing spinal medication or catheter insertion into the subarachnoid CSF space. The needle of the present invention can also be used for purposes other than spinal taps and administering medication to the spinal area. The needle of the present invention provides two lumina which are effectively two passages into and/or out of the body through one insertion and such passages are so contoured as to be directed away from each other. Once within the body, such a needle could have application in a number of branches of medicine.

While the present invention has been described in terms of preferred embodiments and particular applications, substitution in detail and design by one skilled in the art can be made without departing from the spirit of the invention.

What I claim is:

1. A multi-lumen epidural-spinal needle comprising:
a first lumen having a first axis;
a second lumen having a second axis; and
a tissue piercing point through which said first lumen and said second lumen exit, forming respectively a first opening and a second opening, said first axis and said second axis being parallel, and said openings diverging near said point such that a catheter exiting said first opening will be deflected along a path nearly perpendicular to said needle while said second opening essentially aligns with said second lumen.

2. The multi-lumen needle of claim 1 wherein said first lumen is larger than said second lumen.

3. The multi-lumen needle of claim 2 further comprising a hub in which said first lumen and second lumen terminate.

4. The multi-lumen needle of claim 3 wherein said lumen diverge in said hub.

5. The multi-lumen needle of claim 4 wherein said hub has a first passage communicating with said first lumen and a second passage communicating with said second lumen, said first passage and said second passage diverging at an angle not greater than 15 degrees; and further comprising a flange attached to said hub communicating with said first passage, said flange serving as a syringe adapter and having an index mark.

6. The multi-lumen needle of claim 2 wherein said first lumen and said second lumen are in an over under relationship and are connected by welding.

7. The multi-lumen needle of claim 6 wherein each of said lumen are between 14 and 32 gauge.

8. The multi-lumen needle of claim 7 further comprising flanges attached to said hub.

9. The multi-lumen needle of claim 4 further comprising a stop attached to said hub to limit the depth of insertion of the multi-lumen needle thereby avoiding separation of the skin by said diverging lumina.

10. The multi-lumen needle of claim 8 further comprising a color coded polymeric hub assembly to identify the size and tip configuration of the needle.

* * * * *